(12) United States Patent
McCormick

(10) Patent No.: US 6,196,221 B1
(45) Date of Patent: Mar. 6, 2001

(54) THERMAL EXCHANGE BREATHING DEVICE

(75) Inventor: Bruce McCormick, Houston, TX (US)

(73) Assignee: Polar Wrap, LLC, Memphis, TN (US)

( * ) Notice: Subject to any disclaimer, the term of this patent is extended or adjusted under 35 U.S.C. 154(b) by 0 days.

(21) Appl. No.: 09/246,750

(22) Filed: Feb. 8, 1999

(51) Int. Cl.$^7$ .................................................. A61M 16/00
(52) U.S. Cl. .................................. 128/204.17; 128/201.13
(58) Field of Search ........................ 128/200.24, 201.13, 128/204.17, 205.25, 206.12, 206.19, 206.21

(56) References Cited

U.S. PATENT DOCUMENTS

| | | | |
|---|---|---|---|
| 4,905,686 | * 3/1990 | Adams | 128/204.17 |
| 5,435,299 | * 7/1995 | Langman | 128/204.17 |
| 5,570,684 | * 11/1996 | Behr | 128/204.17 |
| 5,906,201 | * 5/1999 | Nilson | 128/204.17 |

* cited by examiner

Primary Examiner—Glenn K. Dawson
(74) Attorney, Agent, or Firm—Reising, Ethington, Barnes, Kisselle, Learman & McCulloch, P.C.

(57) ABSTRACT

A thermal exchange breathing device is provided which include a heat exchange module 14 which is mounted in a face mask (12) with an air flow passage extending from a mouthpiece (72) through a breathing vent (64) to an atmospheric vent (68) through a heat exchange medium (68) in the heat exchange module. The face mask (12) is provided with a head strap (22,94) which may include connectors (95 and 95') between the respective ends of the head strap and the sides of the face mask, said connectors including a stand-off (97) to keep the face mask snug against the user's face when the user wears a helmet.

7 Claims, 2 Drawing Sheets

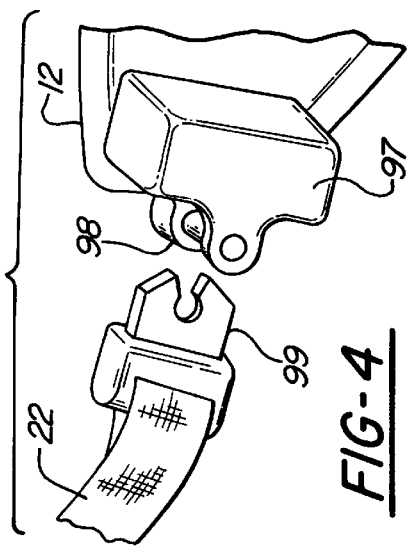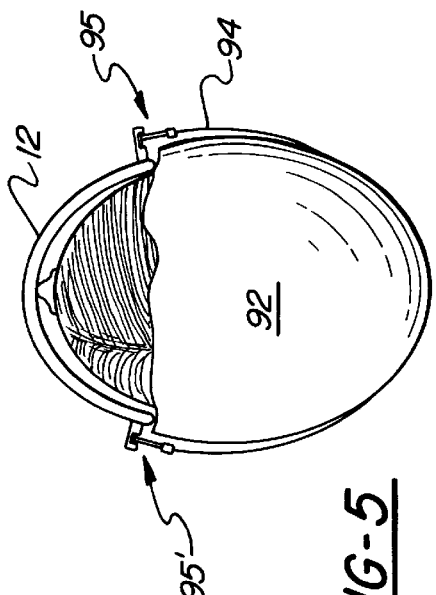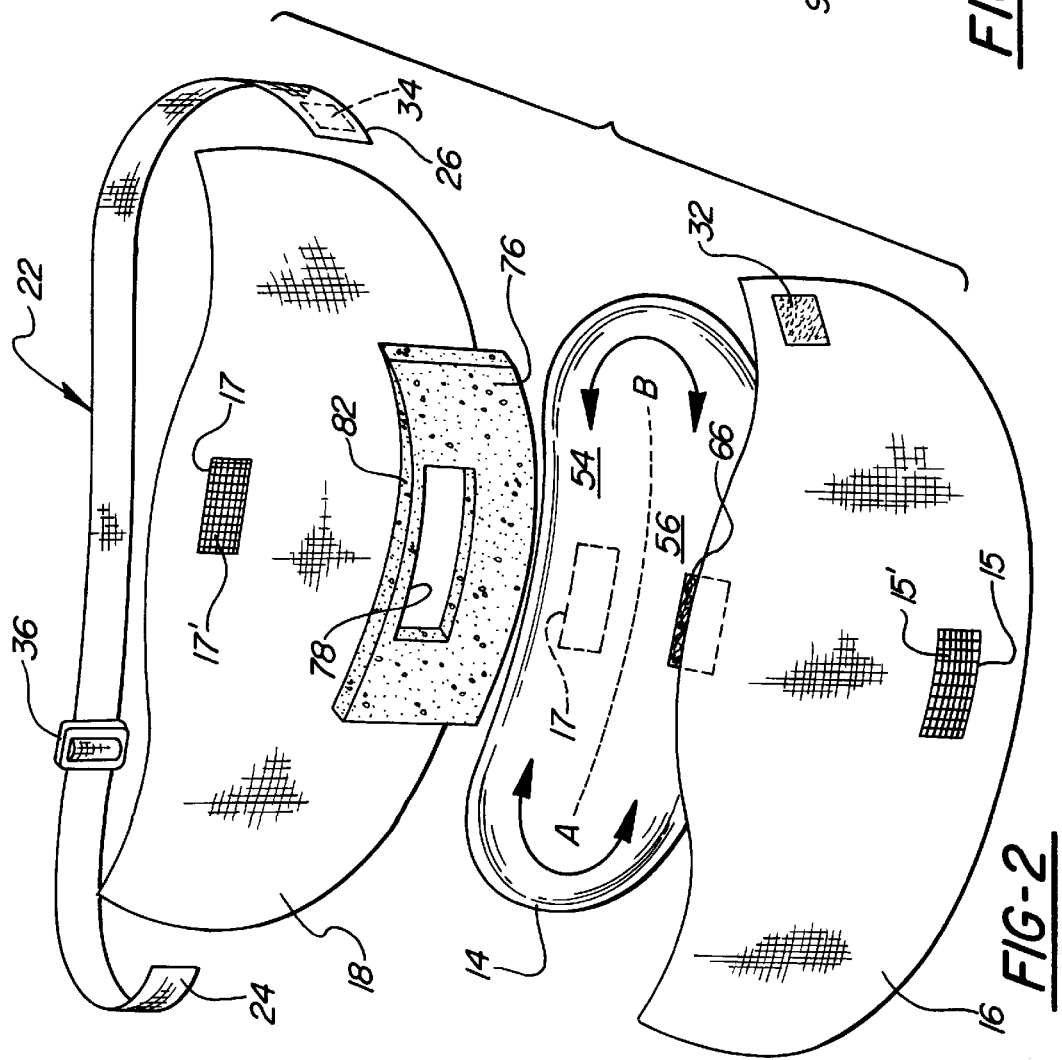

THERMAL EXCHANGE BREATHING DEVICE

FIELD OF THE INVENTION

This invention relates to cold weather breathing apparatus and more particularly, it relates to the combination of a face mask and a heat exchanger.

BACKGROUND OF THE INVENTION

It has long been recognized that, in cold weather conditions, a significant amount of body heat is lost as a result of the inhalation of cold, dry air. This can result in discomfort in milder conditions and be a serious health hazard in arctic or sub-arctic conditions.

U.S. Pat. No. 5,706,802 granted Jun. 13, 1998 to McCormick discloses a cold weather breathing device with a heat exchanger module mounted in a cloth face mask. The heat exchanger module of this patent is of such design that it is very compact and light weight and yet has an elongated flow passage for the inflow and outflow of the breath of the user. The device provides high thermal efficiency in the transfer of heat to and from the breath of the user and yet it does not interpose a significant impedance to the flow of breath through the medium of the heat exchanger.

It is desirable to further improve the efficacy of the cold weather breathing device described above. It has been found that the coupling between the mouth of the user and the heat exchanger leaves something to be desired in respect to thermal efficiency and in respect to fitting of the mask to the user's face for eliminating dead air space, ease of breathing and comfort.

There are several prior art devices which address the problem of using the heat from exhaled air to warm inhaled air. For example, U.S. Pat. Nos. 4,458,679 granted Jun. 10, 1984 to Ward and 4,196,728 granted Apr. 8, 1980 to Granite disclose breathing devices including air inlet and outlet ports, a flow path therebetween, and a heat exchanging medium within the flow path for retaining the heat and humidity from exhaled air to warm and humidify inhaled air. Similarly, U.S. Pat. No. 4,150,671 granted Apr. 24, 1979 to Tiger discloses a mask including separate and concentric air inlet and outlet passages with heat exchanging fins surrounding the air inlet passage and disposed within the outlet passage for permitting the exchange of heat therebetween. U.S. Pat. No. 5,058,211 granted Oct. 22, 1991 to Hanks discloses a bandanna-type device to be wrapped around the face of a user including a strip of thermally insulative material retained within the bandanna and positioned adjacent the mouth of a user.

A general object of this invention to provide a combined face mask and heat exchanger with improved air flow and thermal coupling between the user's mouth and the heat exchanger and to overcome certain other disadvantages of the prior art.

SUMMARY OF THE INVENTION

In accordance with this invention, a thermal exchange device is provided with an improved structural arrangement of the heat exchange module and the face mask incorporating the module.

Further, in accordance with this invention, an improved air flow coupling is provided between the mouth of the user and the breathing vent of the heat exchanger. This is accomplished by providing a mouthpiece or lip pocket for coupling the user's mouth with the breathing vent of the heat exchanger.

Further, in accordance with this invention, a pad is interposed between the inner panel of the face mask and the heat exchanger with a mouthpiece formed in the pad opposite the breathing vent to position the mouth in close proximity to the vent and to provide sealing of the flow path of the breath.

Further, in accordance with this invention, an improved thermal exchange coupling is provided between the user's mouth and the heat exchange medium by providing a mouthpiece opposite the breathing vent of the heat exchanger to facilitate the placement of the user's mouth in alignment with the vent and thus eliminate dead air space from the coupling path.

Further, in accordance with this invention, a close fit of the face mask with the user's face is achieved by providing a foam pad between the inner panel of the face mask and the heat exchanger module with the upper edge of the foam pad defining a notch which will accommodate the user's nose.

Further, in accordance with this invention, a close fit of the face mask is achieved when the user wears a helmet, such as a skier's helmet, by providing a head strap having each end connected with one side of the face mask through a stand-off.

A complete understanding of this invention will be obtained from the description that follows taken with the accompanying drawings.

DESCRIPTION OF THE DRAWINGS

FIG. 2 is an exploded view of the face mask and heat exchanger module;

FIGS. 4 and 5 show a modified head strap connection to provide a snug fit of the face mask on a user wearing a helmet.

BEST MODE FOR CARRYING OUT THE INVENTION

Figure 3:
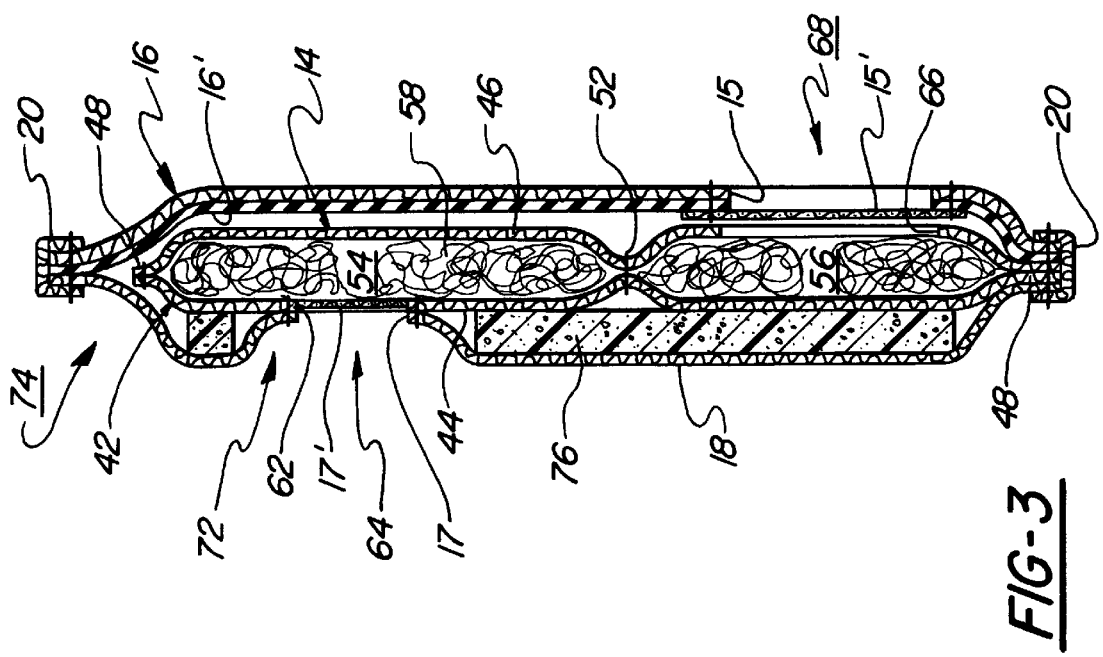
FIG. 3 is a sectional view of the thermal exchange breathing device.

Referring now to the drawings, there is shown an illustrative embodiment of the invention in a breathing device comprising a combination of a heat exchanger module and a face mask. It will be appreciated, as the description proceeds, that this invention may be used in other applications and may be realized in different embodiments.

Figure 1:
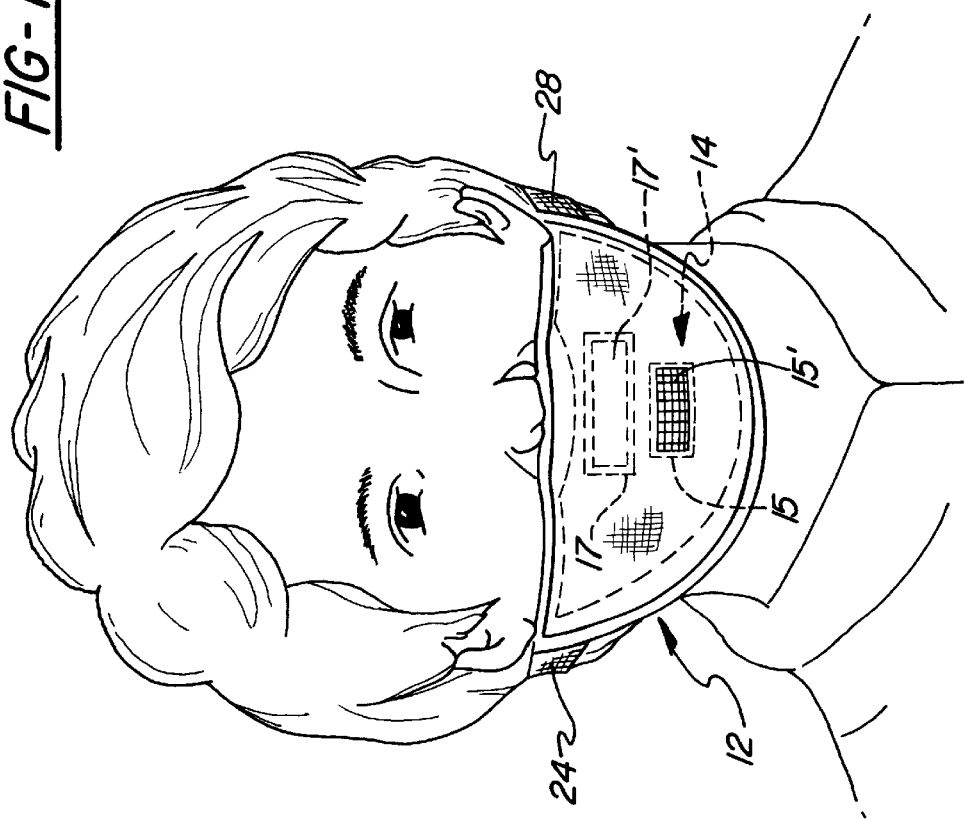
FIG. 1 shows the thermal exchange breathing device of this invention on the face of the user.

FIG. 1 shows the breathing device of this invention on the face of a user. The breathing device 10 comprises the combination of a face mask 12 and a heat exchanger module 14.

FIGS. 2 and 3 show the face mask 12 and heat exchanger module 14 in greater detail. The face mask 12 comprises a front panel 16 and a rear panel 18 which are connected together around the respective peripheries thereof by a border seam 20 suitably made by stitching. The rear panel 18 is preferably made of brushed polypropylene which is a hydrophobic material and it is treated with an antimicrobial substance. The front panel 16 is preferably constructed of Lycra™ fabric with a neoprene layer 16' on the inside surface so that it is windproof and waterproof. The face mask includes a head strap 22, suitably elastic, which has one end 24 fixedly secured to one side of the face mask. The other end 26 of strap 22 is detachably connected with the other side of the face mask by a hook-and-loop fastener 28, such as Velcro™, comprising a hook-element patch 32 on the front panel 16 and a loop-element patch 34 on the end of the strap. The length of the strap 22 is adjustable by a conventional slideable connector 36.

The mounting of the heat exchanger 14 in the mask 12 will be described in greater detail with reference to FIG. 3. The front panel of 16 of the mask 12 is provided with a rectangular opening 15 which is covered by a Nylon™ screen 15' secured by stitching to the front panel. The rear panel 18 is provided with a rectangular opening 17 which is covered by a nylon screen 17' secured to the rear panel. The heat exchanger module 14 is disposed between the front and rear panels 16 and 18 of the mask, and is mounted in a predetermined position relative to the opening 15 and the opening 17 in the front and rear panels, respectively, as will be described below.

The heat exchanger module comprises an envelope 42 formed of a rear fabric sheet 44 and a front fabric sheet 46. The fabric sheets are preferably made of closed cell neoprene and are stitched together to form a border seam 48 which closes the envelope 42 around the entire periphery of the envelope. The seam 48 is incorporated into the border seam 20 along a portion of the bottom of the envelope 42 but the border seams 48 and 20 are separate around the remainder of the envelope. The front and rear fabric sheets 44 and 46 are connected together along an inside seam 52 which extends horizontally part of the way across the envelope 42. Seam 52 divides the envelope 42 into upper and lower compartments 54 and 56, respectively. The compartments are connected together through flow passages designated by the arrows A and B. The envelope 42 is filled with a heat exchanging medium 58 comprising a substantially uniform dispersion of copper fibers in a woven copper cloth. The rear fabric sheet 44 of the envelope 42 is provided with a rectangular opening 62 which is of the same size as the opening 17 and in alignment therewith. The borders of the two openings 17 and 62 are stitched together and define a rectangular breathing vent 64 which is covered by a screen 17'. The front fabric sheet 46 of the envelope 42 is provided with a rectangular opening 66 which is of the same size as the opening 15 in the front panel 16 and in alignment therewith. A screen 15' covers the opening 15 in the front fabric sheet 46 and is stitched to the sheet. Thus, an atmospheric air vent 68 is defined by the aligned rectangular openings 15 and 66 in the front fabric sheet 46 and in the front panel 16 of the mask, respectively.

In order to provide improved coupling between the mouth of the user and the heat exchanger module 14, a mouthpiece 72 for receiving the user's lips is provided adjacent the breathing air vent 64. Also, in order to provide for close fitting engagement of the mask 18 with the user's face in the vicinity of the nose, a nose recess 74 is provided above the mouthpiece 72. To form the mouthpiece and nose recess, a pad 76 comprised of foam plastic is disposed between the rear panel 18 of the face mask and the rear fabric sheet 44 of the heat exchanger envelope 42. The pad 76 is of uniform thickness and is provided with an oblong aperture 78 which is sized to encompass the user's lips. The pad 76 is positioned relative to the breathing air vent 64 so that the aperture 78 surrounds the air vent. The stitching of the rear panel 18 to the rear fabric sheet 44 holds the fabric of the rear panel in a cup-like configuration to form the mouthpiece 72 within the confines of the aperture 78 in the pad 76. The pad 76 has an arc-shaped notch in the upper edge 82 such that the upper edge extends to a higher level at the opposite ends of the pad than it does in the center of the pad. Thus, the fabric of the rear panel 18 is pulled by the seam 20 so that it forms a nose recess 74 in the shape of a quarter-moon across the upper edge of the face mask.

With the face mask 12 positioned on the user's face as shown in FIG. 1, the user's lips are positioned in the mouthpiece 72 and the tip of the user's nose is positioned in the nose recess 74. The visible appearance of the mouthpiece and the nose recess greatly facilitates the positioning of the mask on the user's face for comfort and for optimizing ease of breathing and thermal coupling with the heat exchanger 14.

It will be understood that the user's breath, upon both inhaling and exhaling, passes through the breathing vent 64 and the atmospheric air vent 68 through the heat exchanging medium 58. The air flow between the breathing air vent 64 and the atmospheric air vent 68 extends through the two non-linear U-shaped paths A and B (FIG. 2). This provides an elongated flow paths through the heat exchanging medium to thereby optimize the heat exchange between the user's breath and the medium.

FIG. 5 depicts the use of the breathing device of this invention by a user wearing a helmet 92. FIG. 5 is a view looking down at the top of the user's head with the front portion of the helmet cut-away to reveal the breathing device 12 (in a top elevation view) with the device being held snugly against the user's nose and cheeks by a head strap 94. The head strap 94 is suitably of construction similar to that of head strap 22 with a slideable connector for adjusting the length of the head strap. Connectors 95 and 95', of two-part construction, are provided to connect opposite ends of the strap 94 to opposite sides of the face mask 12. The connectors 95 and 95' are suitably of the same construction and accordingly the description will be given with reference to connector 95 only. The two-part connector 95 is shown in detail in FIG. 4. It comprises a stand-off 97 in the form of a molded plastic block secured to the side of the face mask 12, as by bonding or riveting. The stand-off 97 incorporates socket 98 of the connector 95. The blade 99 of the connector 95, made of molded plastic, is attached to the end of the strap 22. The connector 95 is incorporated into the stand-off 97 so that the strap is connected at a location on the stand-off which is spaced outwardly, i.e. away from the user's head, from the point of connection of the stand-off to the face mask. As a result, the pulling force of the strap which is applied through the stand-off 97 to the face mask 12 is in a direction which holds the face mask against the face of the user instead of pulling it outwardly from the face of the user. The connectors 95 and 95' are adapted for manual connection by thrusting the blade 99 into the socket 98 and for detachment by manual pulling of the blade from the socket. The connectors 95 may be of other suitable design such as the Fastex™ connector disclosed in U.S. Pat. Nos. 4,150, 464 and 4,171,555. It will be apparent that only one of the connectors 95 and 95' need be detachable and accordingly the other may be of any conventional design for fixedly connecting the end of the head strap 22 to the stand-off 97.

Although the description of this invention has been given with reference to a particular embodiment, it is not to be construed in a limiting sense. Many variations and modifications will now occur to those skilled in the art. For a definition of the invention, reference is made to the appended claims.

What is claimed is:

1. A breathing device comprising:
    a heat exchanger module including a container with a wall surrounding an interior space and defining at least one flow passage having first and second ends,
    a breathing vent disposed through said wall for inflow and outflow of air relative to said first end of said flow passage, an atmospheric vent disposed through said wall for both inflow and outflow of air relative to said second end of said tubular flow passage, a heat exchanging medium disposed within said flow passage, a face mask supporting said heat exchanger module and adapted to retain it in a position adjacent the face of a user, said face mask comprising rear and front flexible panels defining a space therebetween, a first opening in the rear panel located in a position for alignment with the mouth of said user, said heat exchanger module disposed between the rear and front panels with the breathing vent located opposite the first opening, a second opening in the front panel located in alignment with the atmospheric vent, a pad disposed between the heat exchanger module and the rear panel, said pad defining an aperture in alignment with said breathing vent, said aperture having a peripheral edge of such configuration as to substantially encompass the mouth of said user, said pad having a thickness to accommodate the lips of said user, said rear panel covering said peripheral edge of said aperture to thereby provide a mouthpiece coupled with said breathing vent, whereby the breathing vent may be readily positioned in front of the user's mouth with a seal between said mouthpiece and the peripheral edge of the user's mouth and whereby the dead air space between said user's mouth and the breathing air vent is minimized to improve the thermal efficiency of the heat exchanger.

2. A breathing device as defined in claim 1 wherein said pad is foam plastic.

3. A breathing device as defined in claim 1 wherein the upper edge of the pad defines a notch in a position opposite the nose of the user.

4. A breathing device as defined in claim 1 including:

an adjustable strap with opposite ends thereof connected to opposite sides of the face mask.

5. A breathing device as defined in claim 4 wherein:

one end of the strap is removably attached to the face mask by a hook-and-loop fastener.

6. A breathing device as defined in claim 4 wherein:

one end of the strap is provided with a slideable connector for adjusting the length of the strap.

7. A breathing device as defined in claim 4 including:

a standoff attached to each side of the face mask, said adjustable strap having each end connected to one side of the face mask through said standoff.

* * * * *